(12) United States Patent
Garnett

(10) Patent No.: US 6,359,008 B1
(45) Date of Patent: Mar. 19, 2002

(54) ACYLATED AMINOACIDS FOR INCREASING THE UPTAKE OF SELECTED SUBSTANCES BY ORGANISMS

(75) Inventor: David J. Garnett, Wales (GB)

(73) Assignee: Lovesgrove Research Limited (GB)

( * ) Notice: Subject to any disclaimer, the term of this patent is extended or adjusted under 35 U.S.C. 154(b) by 0 days.

(21) Appl. No.: 09/623,278
(22) PCT Filed: Mar. 3, 1999
(86) PCT No.: PCT/GB99/00627
§ 371 Date: Nov. 20, 2000
§ 102(e) Date: Nov. 20, 2000
(87) PCT Pub. No.: WO99/44986
PCT Pub. Date: Sep. 10, 1999

(30) Foreign Application Priority Data

Mar. 5, 1998 (GB) ................................. 9804552

(51) Int. Cl.$^7$ ............................................... A01N 37/18
(52) U.S. Cl. ........................ 514/613; 514/946; 554/63
(58) Field of Search ................... 554/63; 514/613, 514/949

(56) References Cited

U.S. PATENT DOCUMENTS 4,442,090 A * 4/1984 Nobuharu et al.

FOREIGN PATENT DOCUMENTS

| FR | 2751177 | * 1/1998 |
| WO | WO90/14429 | 11/1990 |
| WO | WO92/20647 | 11/1992 |
| WO | 92/20647 | * 11/1992 |

OTHER PUBLICATIONS

International Search Report for PCT/GB99/00627, Jul. 21, 1999.

Epand et al., *Biochimica Biophysica Atca*, vol. 1373, Properties of lipoamino acids incorporated into membrane bilayers, XP–002109369, pp. 67–75, 1998.

* cited by examiner

Primary Examiner—Deborah D. Carr
(74) Attorney, Agent, or Firm—Thompson Coburn LLP

(57) ABSTRACT

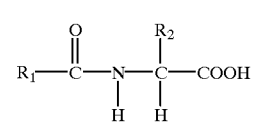

An acylamino acid for enhancing the bio-availability of substances in organisms by permeabilization of cell membranes, the acylamino acid having general formula (I) wherein $R_1$ is hydrogen, a primary, secondary or tertiary alkyl or alkenyl group and $R_2$ is hydrogen, a straight or branched chain alkyl group or a straight or branched chain substituted alkyl group, the substituted being selected from thio, thioether, hydroxy, carboxy, quarternary ammonium, amide, heterocyclic, benzyl, substituted benzyl, amino, substituted amino groups and difunctional alkyl groups linking to the nitrogen atom. A preferred acylamino acid for incorporating into an animal or fish feed is 2-palmitoylaminoproprionic acid.

20 Claims, 3 Drawing Sheets

Figure 1:
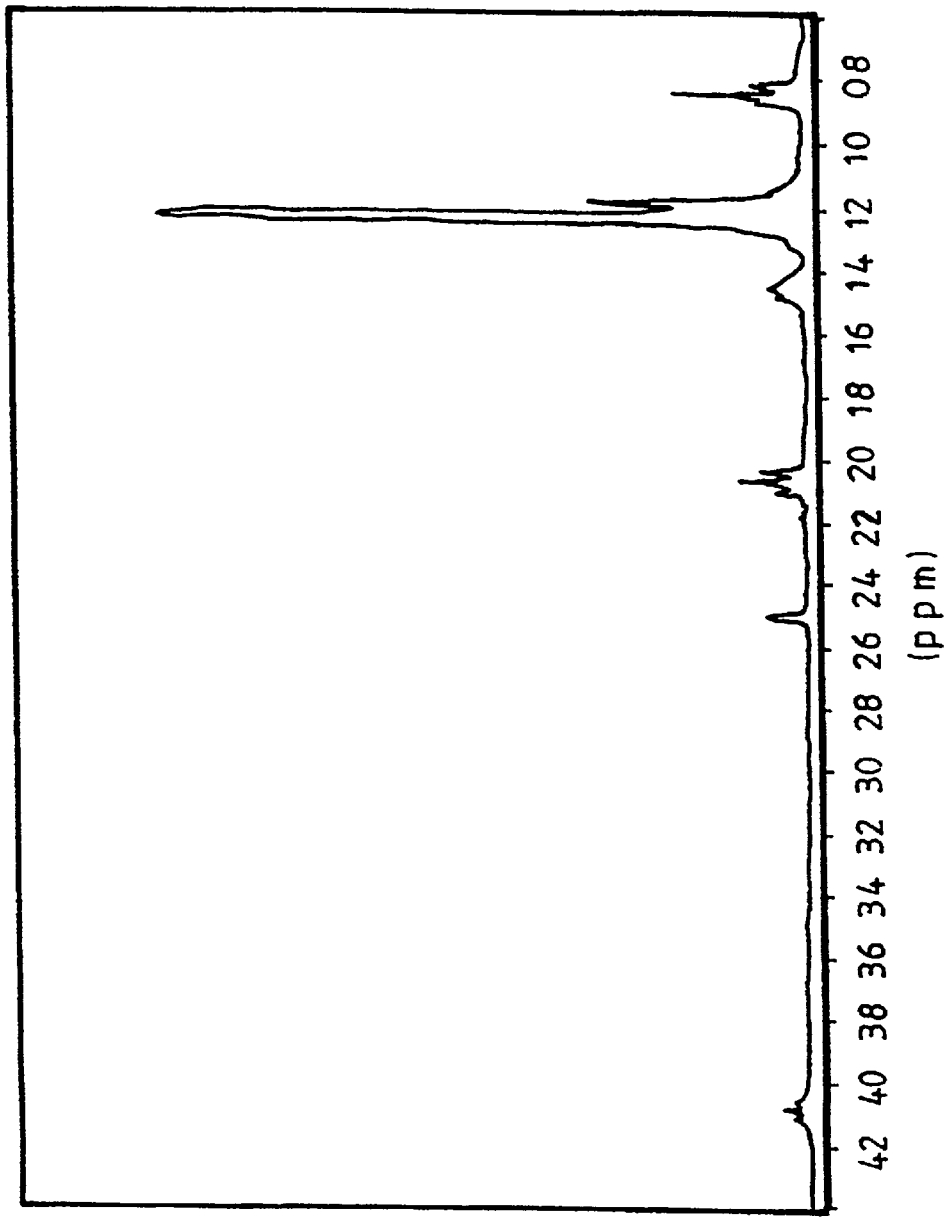

ACYLATED AMINOACIDS FOR INCREASING THE UPTAKE OF SELECTED SUBSTANCES BY ORGANISMS

This applications is a 371 of PCT/GB99/00627 filed Mar. 3, 1999.

DESCRIPTION

The present invention relates to organic compounds for providing improved bioavailability of drugs and nutrients by permiabilising cell membranes of organisms, in particular animals and fish. The improved organic compounds may be used as an animal or fish feed additive to increase, for example, nutrient and pigment uptake.

Previously lysophospholipids and phospholipids have been added to animal feeds to act as growth enhancers by increasing the uptake of nutrients, to increase pigment absorption and for the nanoencapsulation of drugs for drug delivery in vivo. For example, International Patent Application No. PCT/GB93/00736 in the name of David Garnett describes an animal feed containing a substantially pure lipophilic, phospholipid component which is introduced into the stomach cell membrane of an animal to increase the porosity of the membrane.

Lysophospholipids and phospholipids are available as purified natural compounds and as a result are substantially impure. Thus, artificial organo-phosphorous compounds have been synthesised for use as an animal feed by reaction of a long chain alkyl acid chloride with an organophosphonic acid derivative, as described in GB231191A and PCT/GB97/01020.

However, the use of such organophosphorous compounds as animal feed additives has a number of drawbacks. Firstly, the synthesis of pure organophosphorous compounds is expensive and difficult to prepare on a large scale. Additionally, the use of compounds containing a valence five phosphorous as a feed additive is environmentally unfriendly and may have toxicological effects on the organism to which it has been administered.

It is an object of the present invention to provide improved organic compounds for use as feed additives which overcome the abovementioned drawbacks for increasing the uptake of selected compounds, such as nutrients and pigments.

Accordingly, the present invention provides a fish feed additive comprising an acylamino acid for combining with a substance to enhance the bio-availability of thate substance in the fish by permabilisation of cell membranes of the fish, the acylamino acid having the general formula:

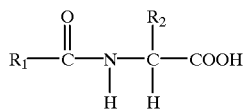

wherein
$R_1$ is hydrogen, a primary, secondary or tertiary alkyl or alkenyl group and
$R_2$ is hydrogen, a straight or branched chain alkyl group or a straight or branched chain substituted alkyl group, the substituents being selected from thio, thioether, hydroxy, carboxy, quarternary ammonium, amide, heterocyclic, benzyl, substituted benzyl, amino, substituted amino groups and difunctional alkyl groups linking to the nitrogen atom of the peptide bond.

Preferably, $R_1$ is a long chain alkyl group having at least 10 carbon atoms. For example, being a lauroyl $(CH_3(CH_2)_{10})$, palmitoyl $(CH_3(CH_2)_{14})$ or a stearoyl group $(CH_3(CH_2)_{16})$. Alternatively, $R_1$ may be a long chain alkenyl group, such as an oleate $(CH_3(CH_2)_7CH=CH(CH_2)_7)$. $R_2$ may be the side chain of any amino acid but preferably is a short chain alkyl group having 1 to 4 carbon atoms, such as a methyl or ethyl group.

A preferred acyl amino acid for incorporating into the feed additive of the present invention is 2-palmitoylaminoproprionic acid.

The compound may be in the form of a powder for incorporation into the feed, for example being mixed with a suitable carrier such as silica talc, be in the form of capsules or be dissolved in water for drinking.

The substance that combines with the acylaminoacid to enhance its bioavailability is preferably a pigment.

The compound is preferably provided in synthetic form.

The present invention will now be further illustrated by means of the following Example and accompanying drawings.

It has been found that acyl amino acids increase the uptake of selected compounds into organisms by permabilising the cell membrane. The acyl amino acids preferably contain a long chain alkyl or alkenyl group, such as a palmitoyl or oleate group led to an amino acid, such as glycine, alanine, valine, threonine or methionine.

The present invention will now be further illustrated by means of the following Example and accompanying drawings.

The acyl amino acid, 2-palmitoylaminoproprionic acid or palmitoyl alanine has been found to increase the uptake of selected compounds, in particular pigments in organisms such as fish. The high polar head group appears to provide the bio-activity of the compound without having to incorporate a phosphonic group therein. Surprisingly, the compound is heat stable to approximately 130° C. even though the structure does not confer a C—P bond which is thought to confer the required thermal stability to related phosphonic compounds.

The compound may be prepared using the Schotten-Baumann procedure. Palmitoyl chloride (44.0 g, 0.16 mol) is added dropwise to a solution of DL-alanine (21.4 g, 0.24 mol) in 10% aqueous sodium hydroxide (200 ml) heated at 50° C. The pH of the reaction is monitored such that the pH does not drop below 10. After the addition is complete, the reaction is stirred for a further 1 hour before it is allowed to cool to room temperature and neutralised with concentrated hydrochloric acid. The resultant precipitate is collected by filtration, washed with water and allowed to dry in air. The product is recrystallised from ether-petrol to give 2-palmitoylaminoproprionic acid as a white solid (36.4 g, 70%).

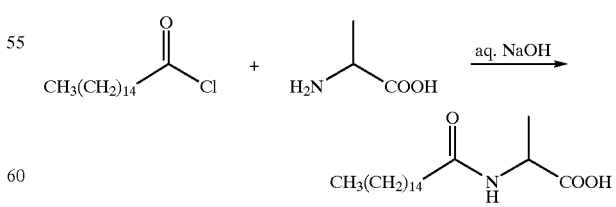

Scheme

Figure 2:
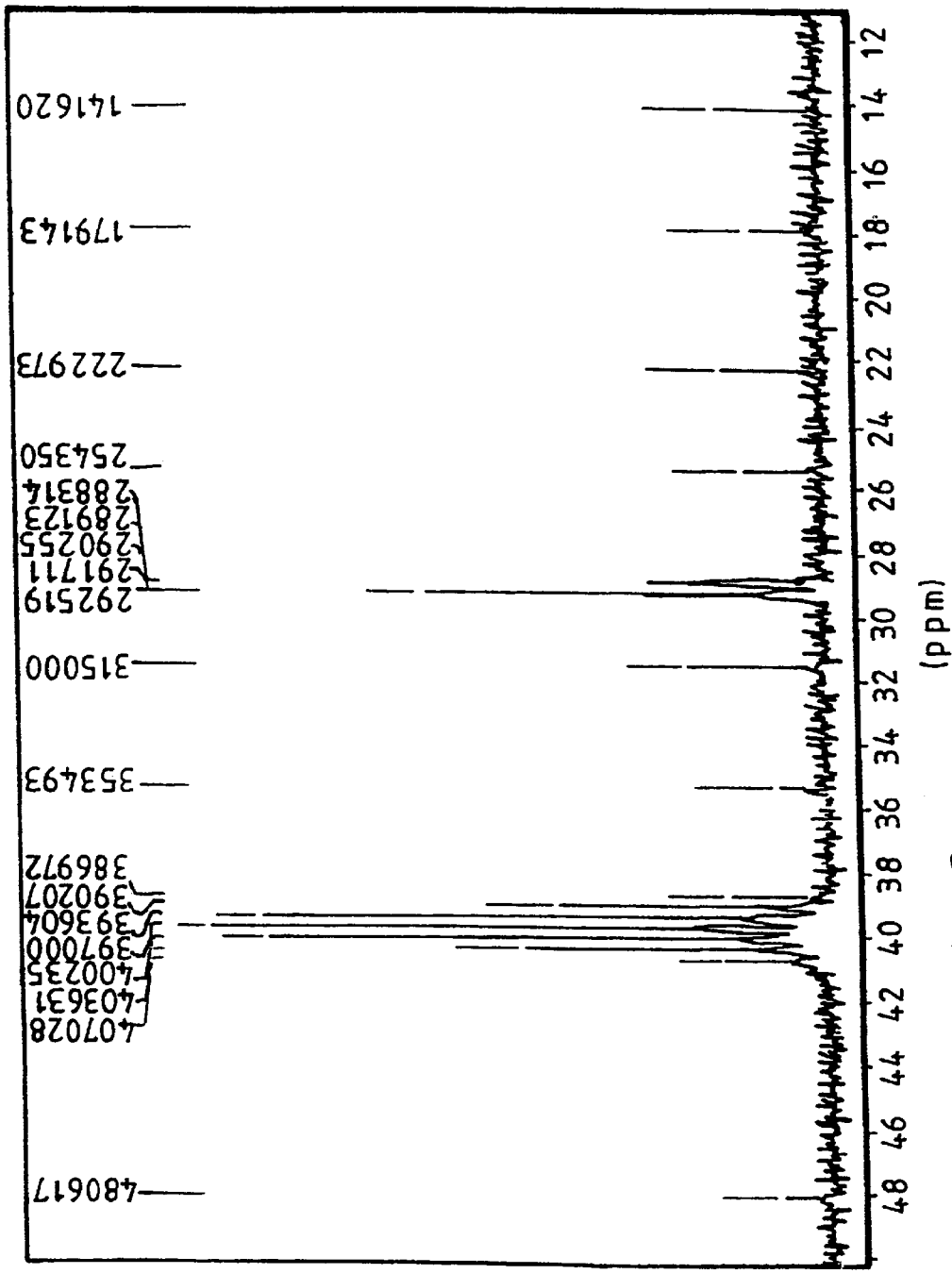

FIGS. 1 and 2 of the accompanying drawings provide the 1H NMR spectrum and $^{13}C$ NMR spectrum of the product.

$^1H$ NMR (DMSO-$d_6$) δ0.85, t, J=7.2 Hz, 3H, RCH$_3$; 1.19, bm, 27H, 12×CH$_2$, CH$_3$; 1.45, m, 2H, CH$_2$CH$_2$CO; 2.06, t, J=7.2 Hz, 2H, CH$_2$CO; 4.07,m, 1H, CHCOOH.

$^{13}$C NMR (DMSOd$_6$) δ14.16; 17.91; 22.30; 25.43; 28.83; 28.91; 29.02; 29.17; 29.25; 31.50; 35.34; 48.06.

A field trial was conducted at a fish farm facility adjacent to the Rheidol hydroelectric station to establish a preliminary indication of the efficacy of Corbinol comprising 75 g palmitoylaminoproprionic acid with 925 g of silica talc carrier as a pigment adsorption enhancer. Approximately 250 Rainbow Trout were divided into two groups and held in separate tanks each 4 m×4 m×1 m. The fish were hand fed for a duration of 4 weeks, the diets for the two groups being:

Control: Mainstream Trout Hi-Performance 40

Treated: Mainstream Trout Hi-Performance+Corbinol (1 kg/tonne) At the end of the trial 100 farm fish from each group were removed and individually weighed. Equal levels of flesh samples were bulked together forming 10 groups of 10 for both the control and treated diets. HPLC analysis was conducted using a Merck-Hitachi L-4250 UV-Vis detector following an isocratic method referred to in a Roche Ltd publication. The results are summarised in Table 1 below.

TABLE 1

|  | CONTROL | TREATED |
| --- | --- | --- |
| FISH WEIGHT (g, mean ± 95% confidence interval) | 331 ± 21 | 352 ± 27 |
| ASTAXANTHIN (mg/kg, mean ± 95% confidence interval) | 1.91 ± 0.10 | 2.06 ± 0.13 |

Figure 3:
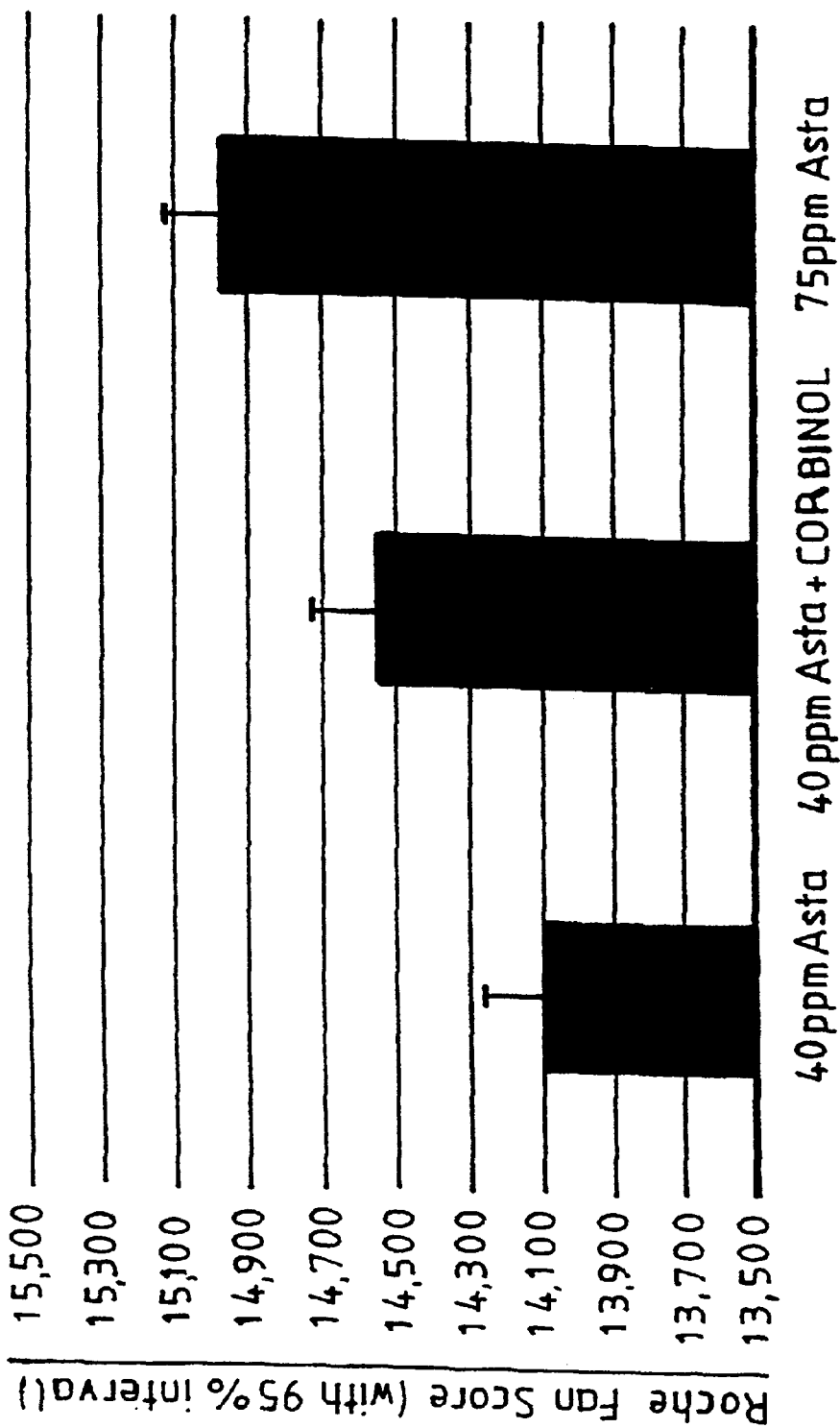

FIG. 3 of the accompanying drawings illustrates the results of a further field trial conducted on Rainbow Trout administered with the following diets:

−ve Control Diet: Trouw Royale Supreme+40 Asta

Treated Diet: Trouw Royale Supreme+40 Asta+Corbinol

+ve Control Diet: Trouw Royale Supreme+75 Asta

The results indicate that acyl amino acids may be used to increase the uptake of substances, such as pigments by organisms, such as fish. The use of such compounds in feed additives is preferable since the compounds are more readily available, easier to prepare and less toxic than the previously used phosphonic compounds.

What is claimed is:

1. A method for enhancing the bioavailability of a substance to a fish, the method comprising administering to the fish said substance in combination with the acylamino acid having the general formula:

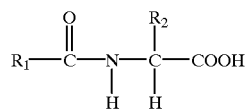

wherein

R$_1$ is hydrogen, a primary, secondary or tertiary alkyl or alkenyl group and

R$_2$ is hydrogen, a straight or branched chain alkyl group or a straight or branched chain substituted alkyl group, the substituents being selected from thio, thioether, hydroxy, carboxy, quarternary ammonium, amide, heterocyclic, benzyl, substituted benzyl, amino, substituted amino groups and difunctional alkyl groups linking to the nitrogen atom of the peptide bond.

2. A method as set forth in claim 1 wherein R$_1$ has at least ten carbon atoms.

3. A method as set forth in claim 2 wherein R$_1$ is selected from the group consisting of (CH$_3$(CH$_2$)$_{10}$)—, (CH$_3$(CH$_2$)$_{14}$)—, and (CH$_3$(CH$_2$)$_{16}$)—.

4. A method as set forth in claim 1 wherein R$_1$ corresponds to (CH$_3$(CH$_2$)$_7$)CH=CH(CH$_2$)$_7$—.

5. A method as set forth in claim 1 wherein R$_2$ has 1 to 4 carbon atoms.

6. A method as set forth in claim 4 wherein R$_2$ has 1 to 4 carbon atoms.

7. A method as set forth in claim 5 wherein R$_2$ is a methyl or ethyl group.

8. A method as set forth in claim 6 wherein R$_2$ is a methyl or ethyl group.

9. A method as set forth in claim 1 wherein the acylamino acid is 2-palmitoylaminoproprionic acid.

10. A method as set forth in claim 1 wherein the acylamino acid at the time of administration to the fish is in the form of a powder incorporated into a feed containing the substance.

11. A method as set forth in claim 1 wherein the substance and the acylamino acid are administered to the fish by feeding them to the fish.

12. A method as set forth in claim 9 wherein the substance and the acylamino acid are administered to the fish by feeding them to the fish.

13. A method as set forth in claim 11 wherein the substance and the acylamino acid are administered to the fish by feeding to the fish a fish feed comprising the substance and the acylamino acid.

14. A method as set forth in claim 12 wherein the substance and the acylamino acid are administered to the fish by feeding to the fish a fish feed comprising the substance and the acylamino acid.

15. A method as set forth in claim 11 wherein the acylamino acid is in the form of a capsule.

16. A method as set forth in claim 1 wherein the substance is a pigment.

17. A method as set forth in claim 1 wherein the administration to the fish of the acylamino acid increases the uptake of the substance in the fish over that which occurs upon administration of the substance without the acylamino acid.

18. A method as set forth in claim 16 wherein the administration to the fish of the acylamino acid increases the concentration of the pigment in the flesh of the fish over that which occurs upon administration of the pigment without the acylamino acid.

19. A method as set forth in claim 17 wherein the substance and the acylamino acid are administered to the fish by feeding them to the fish.

20. A method as set forth in claim 18 wherein the substance and the acylamino acid are administered to the fish by feeding them to the fish.

* * * * *